United States Patent
Chen et al.

(10) Patent No.: US 6,214,760 B1
(45) Date of Patent: *Apr. 10, 2001

(54) CATALYST ACTIVATOR COMPOSITION

(75) Inventors: Eugene Y. Chen, Midland; William J. Kruper, Jr., Sanford; Gordon R. Roof, Midland, all of MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/330,673

(22) Filed: Jun. 11, 1999

Related U.S. Application Data

(60) Provisional application No. 60/096,088, filed on Aug. 11, 1998, and provisional application No. 60/104,229, filed on Oct. 14, 1998.

(51) Int. Cl.$^7$ .............. C07F 17/00; C07F 7/00; B01J 31/00; C08F 4/64
(52) U.S. Cl. ............ 502/103; 502/153; 526/127; 526/160; 526/943; 556/27; 556/52; 556/172; 556/175; 556/179; 556/182
(58) Field of Search ............... 556/27, 52, 175, 556/179, 182, 172; 502/103, 153; 526/127, 160, 943

(56) References Cited

U.S. PATENT DOCUMENTS

| | | | |
|---|---|---|---|
| 5,453,410 | 9/1995 | Kolthammer et al. | 502/155 |
| 5,470,993 | 11/1995 | Devore et al. | 556/11 |
| 5,527,929 | 6/1996 | Timmers et al. | 556/7 |
| 5,556,928 | 9/1996 | Devore et al. | 526/127 |
| 5,602,269 | 2/1997 | Biagini et al. | 556/170 |
| 5,616,664 | 4/1997 | Timmers et al. | 526/127 |
| 5,624,878 | 4/1997 | Devore et al. | 502/152 |

OTHER PUBLICATIONS

Ewen, *Stud. In Surf. Sci. Catal.*, 89, 405–410, (1994).
Bochmann et al., (ACS Dallas Meeting, Mar. 1998, ABS, number INOR 264, subsequently published, *Organometallics*, 1998, 17, 5908–5912).

Primary Examiner—Porfirio Nazario-Gonzalez

(57) ABSTRACT

A composition comprising a mixture of aluminum containing Lewis acids said mixture corresponding to the formula:

$$(Ar^f{}_3Al)(AlQ^1{}_3)_y(-AlQ^2-O-)_z$$

where;

$Ar^f$ is a fluorinated aromatic hydrocarbyl moiety of from 6 to 30 carbon atoms;

$Q^1$ is $C_{1-20}$ alkyl;

$Q^2$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^2$ groups may be covalently linked with each other to form one or more fused rings or ring systems;

y is a number from 0 to 1.0;

z is a number from 0.1 to 20; and the moieties $(Ar^f{}_3Al)(AlQ^1{}_3)_y$ may exist as discrete entities or dynamic exchange products.

15 Claims, No Drawings

CATALYST ACTIVATOR COMPOSITION

CROSS-REFERENCE TO RELATED APPLICATION

This application claims benefit of priority from provisional application Nos. 60/096,088, field Aug. 11, 1998, and 60/104,229, filed Oct. 14, 1998.

BACKGROUND OF THE INVENTION

The present invention relates to compositions that are useful as catalyst activators for olefin polymerizations. More particularly the present invention relates to such compositions that are particularly adapted for use in the coordination polymerization of unsaturated compounds having improved activation efficiency and performance. Such compositions are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of an activator. Generally in the absence of such an activator compound, also referred to as a cocatalyst, little or no polymerization activity is observed.

A class of suitable activators are Lewis acids, especially alumoxanes, which are generally believed to be oligomeric or polymeric alkylaluminoxy compounds, including cyclic oligomers. Examples of alumoxanes (also known as aluminoxanes) include methylalumoxane (MAO) made by hydrolysis of trimethylaluminum as well as modified methylalumoxane (MMAO), wherein a portion of the trimethylaluminum is replaced by a higher alkyl aluminum compound such as triisobutylaluminum. MMAO advantageously is more soluble in aliphatic solvents than is MAO.

Generally alumoxanes contain, on average about 1.5 alkyl groups per aluminum atom, and are prepared by reaction of trialkylaluminum compounds or mixtures of compounds with water (Reddy et al, *Prog. Poly. Sci.*, 1995, 20, 309–367). The resulting product is in fact a mixture of various substituted aluminum compounds including especially, trialklyaluminum compounds (resulting from incomplete reaction of the trialkylaluminum starting reagent or decomposition of the alumoxane). The amount of such free trialkylaluminum compound in the mixture generally varies from 1 to 50 percent by weight of the total product.

Although effective in forming an active olefin polymerization catalyst when combined with a variety of Group 3–10 metal complexes, especially Group 4 metal complexes, generally a large excess of alumoxane compared to metal complex, such as, molar ratios from 100:1 to 10,000:1, is required in order to produce adequate rates of polymerization. Unfortunately, the use of such large excesses of cocatalyst is expensive and also results in polymer having an elevated residual aluminum content. This latter factor may adversely affect polymer properties, especially clarity and dielectric constant.

A different type of activator compound is a Bronsted acid salt capable of transferring a proton to form a cationic derivative or other catalytically active derivative of such Group 3–10, 13 metal complex, cationic charge transferring compounds, or cationic oxidizing activators, referred to collectively hereinafter as cationic activators. Preferred cationic activators are ammonium, sulfonium, phosphonium, oxonium, ferrocenium, silver, lead, carbonium or silylium compounds containing a cation/anion pair that is capable of rendering the Group 3–10 metal complex catalytically active. Preferred anions associated with this cation comprise fluorinated arylborate anions, more preferably, the tetrakis (pentafluorophenyl)borate anion. Additional suitable anions include sterically shielded, bridged diboron anions. Examples of such cationic activators are disclosed in U.S. Pat. Nos. 5,198,401, 5,132,380, 5,470,927, 5,153,157, 5,350,723, 5,189,192, 5,626,087 and in U.S. Pat. No. 5,447, 895, the teachings of which are herein incorporated by reference.

Further suitable activators for activating metal complexes for olefin polymerization include neutral Lewis acids such as tris(perfluorophenyl)borane and tris(perfluorobiphenyl) borane. The former composition has been previously disclosed for the above stated end use in U.S. Pat. No. 5,721, 185, and elsewhere, whereas the latter composition is disclosed in Marks, et al, *J. Am. Chem. Soc.* 1996, 118, 12451–12452. Additional teachings of the foregoing activators may be found in Chen, et al, *J. Am. Chem. Soc.* 1997, 119, 2582–2583, Jia et al, *Organometallics,* 1997, 16, 842–857, and Coles et al, *J. Am. Chem. Soc.* 1997, 119, 8126–8126.

In U.S. Pat. No. 5,453,410, a strong Lewis acid activator, especially tris(pentafluorophenyl)borane, was disclosed for use in combination with constrained geometry metal complexes in combination with an alumoxane. This combination beneficially resulted in effective catalyst activation at molar ratios of alumoxane to catalyst that are much lower than required in the absence of the Lewis acid. Suitably, molar ratios from 1:1 to 50:1 could be employed. In U.S. Pat. Nos. 5,527,929, 5,616,664, 5,470,993, 5,556,928, 5,624,878, the combination of an alumoxane and a strong Lewis acid such as tris(pentafluorophenyl)boron was disclosed as a suitable activator for use with the metal complexes therein disclosed wherein the metal was in the +2 formal oxidation state. It is known that an exchange reaction between aluminum trialkyl compounds and tris(perfluorophenyl)borane occurs under certain conditions. This phenomenon has been previously described in U.S. Pat. No. 5,602,269.

Tris(perfluorophenyl)aluminum is a strong Lewis acid as well. However, it generally performs poorly by itself as an activator compared with tris-(perfluorophenyl)borane at a 1:1 molar ratio with a metal complex. Similarly, It has further been demonstrated that active catalysts resulting from the use of an aluminate anion based upon tris- (perfluorophenyl)aluminum for the activation of ansa-metallocenes and biscyclopentadienyl derivatives of zirconium(IV) are generally of lower activity than those formed by the corresponding borane (Ewen, *Stud. in Surf. Sci. Catal.* 1994, 89, 405–410). A possible explanation for the poor performance of tris-(perfluorophenyl)aluminum as an activator for metallocenes involving a back exchange reaction of a perfluorophenyl group has been proposed by Bochmann et al (ACS Dallas Meeting, March 1998, Abs. number INOR 264, subsequently published, *Organometallics,* 1998, 17, 5908–5912).

In light of these apparent deficiencies, it would be desirable to provide activator compositions based on Lewis acids for activation of metal complexes, especially complexes of metals of Group 4 of the Periodic Table of the elements having improved ease of use, cocatalyst properties and efficiency.

BRIEF DESCRIPTION OF THE INVENTION

According to the present invention there is now provided a composition comprising a mixture of aluminum containing Lewis acids said mixture corresponding to the formula:

$$(Ar^f{}_3Al)(AlQ^1{}_3)_y[(-AlQ^2-O-)_{z'}]_z$$

where;
Ar$^f$ is a fluorinated aromatic hydrocarbyl moiety of from 6 to 30 carbon atoms;

Q$^1$ is C$_{1-20}$ alkyl;

Q$^2$ is C$_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more Q$^2$ groups may be covalently linked with each other to form one or more fused rings or ring systems;

y is a number from 0 to 3.0; preferably from 0 to 1.5, more preferably from 0 to 1.1, and most preferably from 0 to 0.5; and z is a number from 0.01 to 10, preferably from 0.01 to 5, more preferably from 0.01 to 3.5 and the moiety $(-AlQ^2-O-)_{z'}$ is a cyclic or linear oligomer with a repeat unit, z', of 2–30.

It should be furthermore understood that the complex mixture: $(Ar^f{}_3Al)$, $(AlQ^1{}_3)_y$, and $[(-AlQ^2-O-)_{z'}]_z$, may exist as discrete entities or as dynamic exchange products.

Additionally according to the present invention there is provided a catalyst composition that is activated for polymerization of olefins comprising the above identified composition comprising a mixture of Lewis acids and a metal complex. The compositions are capable of forming unique bis μ-bridged adducts with Group 4 metal complexes, i.e., compounds that are essentially doubly activated, that are useful addition polymerization catalysts.

Even further according to the present invention there is provided a process for polymerization of one or more addition polymerizable monomers comprising contacting the same, optionally in the presence of an inert aliphatic, alicyclic or aromatic hydrocarbon, with the above catalyst composition.

DETAILED DESCRIPTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups.

The present invention is based on the discovery that ligand exchange can occur under certain circumstances between aluminum trialkyl residues (especially trimethylaluminum) associated with an alumoxane, and the ligand groups of other Lewis acids brought in contact therewith. Specifically, the catalyst activators of the invention are readily prepared by combining an alkylalumoxane containing residual quantities of trialkylaluminum compound with a Lewis acid containing fluoroaryl ligands, optionally followed by removing byproducts formed by the ligand exchange, if any. Preferred fluoroaryl ligand sources are tris(perfluoroaryl)boron compounds, which result in trialkylboron ligand exchange products that are relatively volatile and easily removable from the reaction mixture, or tris(perfluoroaryl)aluminum compounds. Most preferably fluoroaryl ligand sources are tris(pentafluorophenyl)boron, or tris-(pentafluorophenyl)aluminum. Although resulting in fewer or no byproducts that are detrimental to the use of the resulting activator composition, the latter Lewis acid is moderately shock sensitive and care must be exercised in its use and it should be retained and used in the form of a solution if possible.

Unlike the exchange process occurring between tris (perfluorophenyl)borane with trialkylaluminum, which produces a trialkylborane and tris-(perfluorophenyl)aluminum, the reaction of tris(perfluorophenyl)borane with quantities of trialkylaluminum present in an alumoxane, gives a complex mixture of reaction products incorporating alumoxane and a dimeric or aluminum exchange adduct of tris-(perfluorophenyl)aluminum with a stoichiometric or substoichiometric amount of aluminum trialkylaluminum. This formation occurs and is enhanced by the use of specific reaction conditions. Generally, formation of the desired mixture of Lewis acids involves prolonged contacting of the foregoing components in a hydrocarbon solvent, preferably an aliphatic hydrocarbon solvent. The exchange reaction can be facilitated by the use of more concentrated solutions of reagents and elevated reaction temperatures.

Contacting times preferably are from 10 minutes to 10 hours, more preferably from 15 minutes to 3 hours. Temperatures of the contacting are generally from 20 to 50° C., preferably from 25 to 35° C. Shorter contacting times are required at higher temperatures than at lower temperatures. Desirably, the contacting is also done prior to addition of a metal complex catalyst, such as a metallocene, in order to avoid formation of further derivatives of the exchange products having reduced catalytic effectiveness.

Advantageously, low levels of boron trialkyl (a possible by-product of the ligand exchange) are present in the compositions of the invention. Suitably, such levels are less than or equal to y, preferably less than y and less than 0.1, where y is as previously defined.

That is, the compositions of the invention preferably comprise a mixture of Lewis acids corresponding to the formula:

$$(A^f{}_3Al)(AlQ^1{}_3)_y(BQ^1{}_3)_w[(-AlQ^2-O-)_{z'}]_z$$

where w is a number greater than or equal to 0 and less than or equal to y, preferably less than y and less than 0.1, and all remaining variables are as previously defined.

Such low levels of boron trialkyl can be obtained by techniques of devolatilization, degassing or similar techniques for removing boron trialkyl by-products or by direct reaction of tris(perfluorophenyl)aluminum and an alumoxane as previously discussed. The latter reaction advantageously produces the desired composition in relatively shorter contact times as well. Use of aromatic solvents is acceptable to the desired exchange reaction, however hydrocarbon solvents promote faster exchange. Preferred hydrocarbon solvents for the exchange reaction are C$_{6-8}$ aliphatic and alicyclic hydrocarbons and mixtures thereof, including hexane, heptane, cyclohexane, and mixed fractions such as Isopar™ E, available from Exxon Chemicals Inc.

It is to be understood that the composition of the invention may be recovered in the form of a solid by removal of solvent or it may be retained in solution, whereupon, the composition comprises the individual Lewis acid compounds and one or more adducted solvents. Additionally, quantities of other exchange products, primarily monoalkylbis-(perfluoroaryl)aluminum species and dialkyl-mono-(perfluoroaryl)aluminum species (represented by the formula $Ar^f_{3-x'}AlQ^1_{x'}$, wherein x' is 1 or 2), or adducts thereof also may be formed in the exchange process and be present in the composition of the invention. Such partially exchanged species are not detrimental to the composition's ability to act as a catalyst activator, but are also not believed to be active as co-catalysts either. They are preferably reduced to as low concentration as possible. Generally, by allowing the exchange reaction to proceed as long as possible, reduced quantities of such species result. Preferred levels for such exchange products are less than 0.1 times the quantity of tris-(perfluoroaryl)aluminum compound, preferably less than 0.05 times the quantity of tris(perfluoroaryl) aluminum compound, and most preferably less than 0.01 times the quantity of tris(perfluoroaryl)aluminum compound. That is, accounting for such exchanged species in the formula for the composition of the invention, there is provided a composition comprising a mixture of aluminum containing Lewis acids said mixture corresponding to the formula:

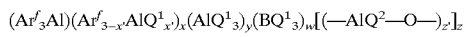

where;

Ar$^f$ is a fluorinated aromatic hydrocarbyl moiety of from 6 to 30 carbon atoms;

$Q^1$ is $C_{1-20}$ alkyl;

$Q^2$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^2$ groups may be covalently linked with each other to form one or more fused rings or ring systems;

w is a number greater than or equal to 0 and less than or equal to y, preferably less than y and less than 0.1;

x' is 1 or 2, x is a number from 0 to 0.1; preferably from 0 to 0.05, more preferably from 0 to 0.01;

y is a number from 0 to 1.0; preferably from 0 to 0.5, more preferably from 0 to 0.2;

z' is a number from 2 to 30; and z is a number from 0.1 to 20, preferably from 0.1 to 5, more preferably from 0.1 to 0.5;.

and $(Ar^f_3Al)$, $(AlQ^1_3)_y$, and $(Ar^f_{3-x'}AlQ^1_{x'})_x$ may exist as discrete entities or as dynamic exchange products Preferred compositions according to the present invention are those wherein Ar$^f$ is pentafluorophenyl, and $Q^1$ and $Q^2$ are $C_{1-4}$ alkyl. Most preferred compositions according to the present invention are those wherein Ar$^f$ is pentafluorophenyl, and $Q^1$ and $Q^2$ are each occurrence methyl and isobutyl. A highly preferred composition according to the present invention is a compound corresponding to the formula: $[Ar^f_y Al_2 Q^1_{(6-y)}][(—AlQ^2—O—)_{z'}]_z$, wherein Ar$^f$, $Q^1 Q^2$, y, z' and z are as previously defined.

In addition to performing the alumoxane exchange process where the starting material is tris(perfluorophenyl)borane, preformed tris(perfluorophenyl)aluminum may be used as an alternative. In this process, the amount of alumoxane required to form a highly activator formula is less than that prescribed for tris(perfluorophenyl)borane. The use of higher ratios of alumoxane to tris (perfluorophenyl)aluminum may lead to lower efficiency in the catalyst polymerization process.

The present composition is a highly active co-catalyst for use in activation of metal complexes, especially Group 4 metallocenes for the polymerization of olefins. In such use it is desirably employed as a dilute concentration in a hydrocarbon liquid, especially an aliphatic hydrocarbon liquid for use as a homogeneous catalyst, especially for solution polymerizations. Additionally, the composition may be deposited on an inert support, especially a particulated metal oxide or polymer, in combination with the metal complex to be activated according to known techniques for producing supported olefin polymerization catalysts, and thereafter used for gas phase or slurry polymerizations.

When in use as a catalyst activator, the molar ratio of metal complex to activator composition is preferably from 0.1:1 to 3:1, more preferably from 0.2:1 to 2:1, most preferably from 0.25:1 to 1:1, based on the metal contents of each component. In most polymerization reactions the molar ratio of metal complex: polymerizable compound employed is from $10^{-12}$:1 to $10^{-1}$:1, more preferably from $10^{-12}$:1 to $10^{-5}$:1.

The reagents employed in the foregoing ligand exchange process, catalyst preparation and use, particularly the alumoxane (as well as the support) should be thoroughly dried prior to use, preferably by calcining at 200–500° C. for a time from 10 minutes to 100 hours.

Suitable techniques for removing alkyl exchange byproducts from the reaction mixture include degassing optionally at reduced pressures, distillation, solvent exchange, solvent extraction, extraction with a volatile agent, contacting with a zeolite or molecular sieve, and combinations of the foregoing techniques, all of which are conducted according to conventional procedures. Purity of the resulting product may be determined by $^{11}$B NMR analysis of the resulting product.

The support for the activator component may be any inert, particulate material, but most suitably is a metal oxide or mixture of metal oxides, preferably alumina, silica, an aluminosilicate or clay material. Suitable volume average particle sizes of the support are from 1 to 1000 μM, preferably from 10 to 100 μM. Most desired supports are calcined silica, which may be treated prior to use to reduce surface hydroxyl groups thereon, by reaction with a silane, a trialkylaluminum, or similar reactive compound. Any suitable means for incorporating the alumoxane/tris-(perfluoroaryl)aluminum cocatalyst mixture onto the surface of a support may be used, including dispersing the cocatalyst in a liquid and contacting the same with the support by slurrying, impregnation, spraying, or coating and thereafter removing the liquid, or by combining the cocatalyst and a support material in dry or paste form and intimately contacting the mixture, thereafter forming a dried, particulated product.

Suitable metal complexes for use in combination with the foregoing cocatalysts include any complex of a metal of Groups 3–10 of the Periodic Table of the Elements capable of being activated to polymerize addition polymerizable compounds, especially olefins by the present activators. Examples include Group 10 diimine derivatives corresponding to the formula:

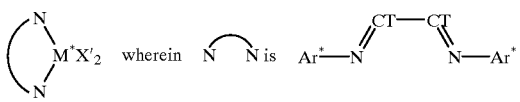

M* is Ni(II) or Pd(II);
X' is halo, hydrocarbyl, or hydrocarbyloxy;
Ar* is an aryl group, especially 2,6-diisopropylphenyl or aniline group; and
CT-CT is 1,2-ethanediyl, 2,3-butanediyl, or form a fused ring system wherein the two T groups together are a 1,8-naphthanediyl group.

Similar complexes to the foregoing are also disclosed by M. Brookhart, et al., in *J. Am. Chem. Soc.*, 118, 267–268 (1996) and *J. Am. Chem. Soc.*, 117, 6414–6415 (1995), as being active polymerization catalysts especially for polymerization of α-olefins, either alone or in combination with polar comonomers such as vinyl chloride, alkyl acrylates and alkyl methacrylates.

Additional complexes include derivatives of Group 3, 4, or Lanthanide metals containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e. g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, and boratabenzene groups, as well as $C_{1-10}$ hydrocarbyl-substituted or $C_{1-10}$ hydrocarbyl-substituted silyl substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands which are boron containing analogues to benzene. They are previously known in the art having been described by G. Herberich, et al., in *Organometallics*, 1995, 14, 1, 471–480. Preferred boratabenzenes correspond to the formula:

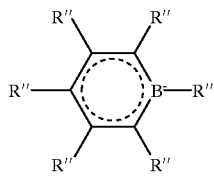

wherein R" is selected from the group consisting of hydrocarbyl, silyl, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Suitable metal complexes for use in the catalysts of the present invention may be derivatives of any transition metal including Lanthanides, but preferably of Group 3, 4, or Lanthanide metals which are in the +2, +3, or +4 formal oxidation state meeting the previously mentioned requirements. Preferred compounds include metal complexes (metallocenes) containing from 1 to 3 π-bonded anionic ligand groups, which may be cyclic or noncyclic delocalized π-bonded anionic ligand groups. Exemplary of such π-bonded anionic ligand groups are conjugated or nonconjugated, cyclic or non-cyclic dienyl groups, allyl groups, and arene groups. By the term "π-bonded" is meant that the ligand group is bonded to the transition metal by means of delocalized electrons present in a π bond.

Each atom in the delocalized π-bonded group may independently be substituted with a radical selected from the group consisting of halogen, hydrocarbyl, halohydrocarbyl, and hydrocarbyl-substituted metalloid radicals wherein the metalloid is selected from Group 14 of the Periodic Table of the Elements. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system or a hydrogenated fused ring system. Suitable hydrocarbyl-substituted organometalloid radicals include mono-, di- and trisubstituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, and decahydroanthracenyl groups, as well as $C_{1-10}$ hydrocarbyl-substituted derivatives thereof. Preferred anionic delocalized π-bonded groups are cyclopentadienyl, pentamethylcyclopentadienyl, tetramethylcyclo-pentadienyl, indenyl, 2,3- dimethylindenyl, fluorenyl, 2-methylindenyl and 2-methyl-4-phenylindenyl.

More preferred are metal complexes corresponding to the formula:

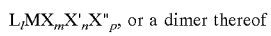L$_l$MX$_m$X'$_n$X"$_p$, or a dimer thereof wherein:

L is an anionic, delocalized, π-bonded group that is bound to M, containing up to 50 nonhydrogen atoms, optionally two L groups may be joined together through one or more substituents thereby forming a bridged structure, and further optionally one L may be bound to X through one or more substituents of L;

M is a metal of Group 4 of the Periodic Table of the Elements in the +2, +3 or +4 formal oxidation state;

X is an optional, divalent substituent of up to 50 non-hydrogen atoms that together with L forms a metallocycle with M;

X' is an optional neutral Lewis base having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 1 or 2;

m is 0 or 1;

n is a number from 0 to 3;

p is an integer from 0 to 3; and the sum, l+m+p, is equal to the formal oxidation state of M.

Such preferred complexes include those containing either one or two L groups. The latter complexes include those containing a bridging group linking the two L groups. Preferred bridging groups are those corresponding to the formula (ER*$_2$)$_x$ wherein E is silicon or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, benzyl, tert-butyl or phenyl.

Examples of the foregoing bis(L) containing complexes are compounds corresponding to the formula:

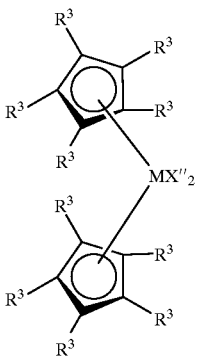

(I)

or

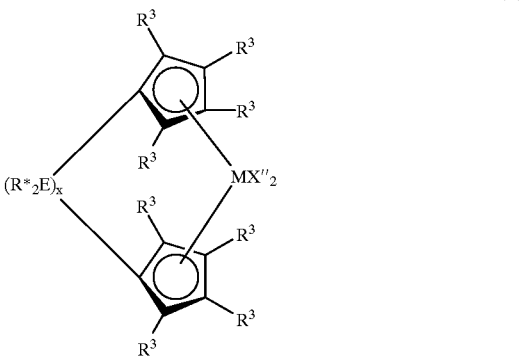

(II)

wherein:
M is titanium, zirconium or hafnium, preferably zirconium or hafnium, in the +2 or +4 formal oxidation state;
R$^3$ in each occurrence independently is selected from the group consisting of hydrogen, hydrocarbyl, silyl, germyl, cyano, halo and combinations thereof, said R$^3$ having up to 20 non-hydrogen atoms, or adjacent R$^3$ groups together form a divalent derivative (that is, a hydrocarbadiyl, siladiyl or germadiyl group) thereby forming a fused ring system, and
X" independently each occurrence is an anionic ligand group of up to 40 nonhydrogen atoms, or two X" groups together form a divalent anionic ligand group of up to 40 nonhydrogen atoms or together are a conjugated diene having from 4 to 30 non-hydrogen atoms forming a π-complex with M, whereupon M is in the +2 formal oxidation state, and
R*, E and x are as previously defined.

The foregoing metal complexes are especially suited for the preparation of polymers having stereoregular molecular structure. In such capacity it is preferred that the complex possess C$_2$ symmetry or possess a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include bis-indenyl complexes. Similar systems based on Ti(IV) or Zr(IV) were disclosed for preparation of isotactic olefin polymers in Wild et al., *J. Organomet. Chem,* 232, 233–47, (1982).

Exemplary bridged ligands containing two π-bonded groups are: (dimethylsilyl-bis-cyclopentadienyl), (dimethylsilyl-bis-methylcyclopentadienyl), (dimethylsilyl-bis-ethylcyclopentadienyl, (dimethylsilyl-bis-t-butylcyclopentadienyl), (dimethylsilyl-bis-tetramethylcyclopentadienyl), (dimethylsilyl-bis-indenyl), (dimethylsilyl- bis-tetrahydroindenyl), (dimethylsilyl-bis-fluorenyl), (dimethylsilyl-bis-tetrahydrofluorenyl), (dimethylsilyl-bis-2-methyl-4-phenylindenyl), (dimethylsilyl-bis-2-methylindenyl), (dimethylsilyl-cyclopentadienyl-fluorenyl), (1,1,2,2-tetramethyl-1,2-disilyl-bis-cyclopentadienyl), (1,2-bis(cyclopentadienyl) ethane, and (isopropylidene-cyclopentadienyl-fluorenyl).

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention correspond to the formula:

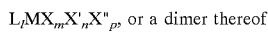

wherein:

L is an anionic, delocalized, π-bonded group that is bound to M, containing up to 50 nonhydrogen atoms;

M is a metal of Group 4 of the Periodic Table of the Elements in the +2, +3 or +4 formal oxidation state;

X is a divalent substituent of up to 50 non-hydrogen atoms that together with L forms a metallocycle with M;

X' is an optional neutral Lewis base ligand having up to 20 non-hydrogen atoms;

X" each occurrence is a monovalent, anionic moiety having up to 20 non-hydrogen atoms, optionally two X" groups together may form a divalent anionic moiety having both valences bound to M or a neutral $C_{5-30}$ conjugated diene, and further optionally X' and X" may be bonded together thereby forming a moiety that is both covalently bound to M and coordinated thereto by means of Lewis base functionality;

l is 1 or 2;

m is 1;

n is a number from 0 to 3;

p is an integer from 1 to 2; and the sum, l+m+p, is equal to the formal oxidation state of M.

Preferred divalent X substituents preferably include groups containing up to 30 nonhydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention correspond to the formula:

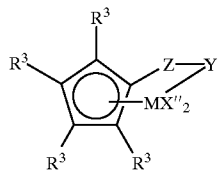

wherein:

M is titanium or zirconium in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system;

each X" is a halo, hydrocarbyl, hydrocarbyloxy or silyl group, said group having up to 20 nonhydrogen atoms, or two X" groups together form a $C_{5-30}$ conjugated diene;

Y is —O—, —S—, —NR*—, —NR*$_2$, —PR*—; and

Z is SiR*$_2$, CR*$_2$, SiR*$_2$SiR*$_2$, CR*$_2$CR*$_2$, CR*=CR*, BNR*$_2$, CR*$_2$SiR*$_2$, or GeR*$_2$, wherein: R* is as previously defined.

Illustrative Group 4 metal complexes that may be employed in the practice of the present invention include:

cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-pentadienyl,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
($\eta^5$-2,4-dimethyl-1,3-pentadienyl)titaniumtrimethyl,
octahydrofluorenyltitaniumtrimethyl,
tetrahydroindenyltitaniumtrimethyl,
tetrahydrofluorenyltitaniumtrimethyl,
(1,1-dimethyl-2,3,4,9,10-η-1,4,5,6,7,8-hexahydronaphthalenyl)titaniumtrimethyl,
(1,1,2,3-tetramethyl-2,3,4,9,10-η-1,4,5,6,7,8-hexahydronaphthalenyl)titaniumtrimethyl,
(tert-butylamido)(tetramethyl-$\eta^5$-cyclopentadienyl) dimethylsilanetitanium dichloride,
(tert-butylamido)(tetramethyl-$\eta^5$-cyclopentadienyl) dimethylsilanetitanium dimethyl,
(tert-butylamido)(tetramethyl-$\eta^5$-cyclopentadienyl)-1,2-ethanediyltitanium dimethyl,
(tert-butylamido)(hexamethyl-$\eta^5$-indenyl) dimethylsilanetitanium dimethyl,
(tert-butylamido)(tetramethyl-$\eta^5$-cyclopentadienyl) dimethylsilane titanium (III) 2-(dimethylamino)benzyl;
(tert-butylamido)(tetramethyl-$\eta^5$-cyclopentadienyl) dimethylsilanetitanium (III) allyl, (tert-butylamido)(tetramethyl-$\eta^5$-cyclopentadienyl) dimethylsilanetitanium (II) 1,4-diphenyl-1,3-butadiene,
(tert-butylamido)(2-methylindenyl)dimethylsilanetitanium (II) 1,4-diphenyl-1,3-butadiene,
(tert-butylamido)(2-methylindenyl)dimethylsilanetitanium (IV) 1,3-butadiene,
(tert-butylamido)(2,3-dimethylindenyl) dimethylsilanetitanium (II) 1,4-diphenyl-1,3-butadiene,
(tert-butylamido)(2,3-dimethylindenyl) dimethylsilanetitanium (IV) 1,3-butadiene,
(tert-butylamido)(2,3-dimethylindenyl) dimethylsilanetitanium (II) 1,3-pentadiene,
(tert-butylamido)(2-methylindenyl)dimethylsilanetitanium (II) 1,3-pentadiene,
(tert-butylamido)(2-methylindenyl)dimethylsilanetitanium (IV) dimethyl,
(tert-butylamido)(2-methyl-4-phenylindenyl) dimethylsilanetitanium (II) 1,4-diphenyl-1,3-butadiene,
(tert-butylamido)(tetramethyl-$\eta^5$-cyclopentadienyl) dimethylsilanetitanium (IV) 1,3butadiene, -butadiene,
(tert-butylamido)(tetramethyl-$\eta^5$-cyclopentadienyl) dimethylsilanetitanium (II) 1,4-dibenzyl-1,3-butadiene,
(tert-butylamido)(tetramethyl-$\eta^5$-cyclopentadienyl) dimethylsilanetitanium (II) 2,4-hexadiene,
(tert-butylamido)(tetramethyl-$\eta^5$-cyclopentadienyl) dimethylsilanetitanium (II) 3-methyl 1,3-pentadiene,
(tert-butylamido)(2,4-dimethyl-1,3-pentadien-2-yl) dimethylsilanetitaniumdimethyl,
(tert-butylamido)(1,1-dimethyl-2,3,4,9,10-$\eta$-1,4,5,6,7,8-hexahydronaphthalen-4-yl) dimethylsilanetitaniumdimethyl,
(tert-butylamido)(1,1,2,3-tetramethyl-2,3,4,9,10-$\eta$-1,4,5,6,7,8-hexahydronaphthalen-4-yl) dimethylsilanetitaniumdimethyl,
(tert-butylamido)(tetramethylcyclopentadienyl) dimethylsilanetitanium 1,3-pentadiene,
(tert-butylamido)(3-(N-pyrrolidinyl)inden-1-yl) dimethylsilanetitanium 1,3-pentadiene,
(tert-butylamido)(2-methyl-s-indacen-1-yl) dimethylsilanetitanium 1,3-pentadiene, and
(tert-butylamido)(3,4-cyclopenta(/)phenanthren-2-yl) dimethylsilanetitanium 1,4-diphenyl-1,3-butadiene.

Bis(L) containing complexes including bridged complexes suitable for use in the present invention include:

biscyclopentadienylzirconiumdimethyl,
biscyclopentadienyltitaniumdiethyl,
biscyclopentadienyltitaniumdiisopropyl,
biscyclopentadienyltitaniumdiphenyl,
biscyclopentadienylzirconium dibenzyl,
biscyclopentadienyltitanium-2,4-pentadienyl,
biscyclopentadienyltitaniummethylmethoxide,
biscyclopentadienyltitaniummethylchloride,
bispentamethylcyclopentadienyltitaniumdimethyl,
bisindenyltitaniumdimethyl,
indenylfluorenyltitaniumdiethyl,
bisindenyltitaniummethyl(2-(dimethylamino)benzyl),
bisindenyltitanium methyltrimethylsilyl,
bistetrahydroindenyltitanium methyltrimethylsilyl,
bispentamethylcyclopentadienyltitaniumdiisopropyl,
bispentamethylcyclopentadienyltitaniumdibenzyl,
bispentamethylcyclopentadienyltitaniummethylmethoxide,
bispentamethylcyclopentadienyltitaniummethylchloride,
(dimethylsilyl-bis-cyclopentadienyl)zirconiumdimethyl,
(dimethylsilyl-bis-pentamethylcyclopentadienyl)titanium-2,4-pentadienyl,
(dimethylsilyl-bis-t-butylcyclopentadienyl) zirconiumdichloride,
(methylene-bis-pentamethylcyclopentadienyl)titanium(III) 2-(dimethylamino)benzyl,
(dimethylsilyl-bis-indenyl)zirconiumdichloride,
(dimethylsilyl-bis-2-methylindenyl)zirconiumdimethyl,
(dimethylsilyl-bis-2-methyl-4-phenylindenyl) zirconiumdimethyl,
(dimethylsilyl-bis-2-methylindenyl)zirconium-1,4-diphenyl-1,3-butadiene,
(dimethylsilyl-bis-2-methyl-4-phenylindenyl)zirconium (II) 1,4-diphenyl-1,3-butadiene,
(dimethylsilyl-bis-tetrahydroindenyl)zirconium(II) 1,4-diphenyl-1,3-butadiene,
(dimethylsilyl-bis-fluorenyl)zirconiumdichloride,
(dimethylsilyl-bis-tetrahydrofluorenyl)zirconiumdi(trimethylsilyl),
(isopropylidene)(cyclopentadienyl)(fluorenyl) zirconiumdibenzyl, and
(dimethylsilylpentamethylcyclopentadienylfluorenyl) zirconiumdimethyl.

Suitable addition polymerizable monomers for use with the foregoing novel catalyst compositions include ethylenically unsaturated monomers, acetylenic compounds, conjugated or non-conjugated dienes, and polyenes. Preferred monomers include olefins, for example alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, isobutylene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ $\alpha$-olefins specifically added to the reaction mixture in order to produce relatively long chain branches in the resulting polymers. Preferably, the alpha-olefins are ethylene, propylene, 1-butene, 1-pentene, 4-methyl-pentene-1, 1-hexene, 1-octene, and combinations of ethylene and/or propene with one or more other alpha-olefins. Other preferred monomers include styrene, halo- or alkyl substituted styrenes, vinylbenzocyclobutene, 1,4-hexadiene, dicyclopentadiene, ethylidene norbornene, and 1,7-octadiene. Mixtures of the above-mentioned monomers may also be employed.

In general, the polymerization may be accomplished under conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Preferred processing conditions include solution polymerization, more preferably continuous solution polymerization processes, conducted in the presence of an aliphatic or alicyclic liquid diluent. By the term "continuous polymerization" is meant that at least the products of the polymerization are continuously removed from the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic α-olefins such as styrene or ring alkyl-substituted styrenes) including toluene, ethylbenzene or xylene, as well as liquid olefins (which may act as monomers or comonomers) including ethylene, propylene, 1-butene, isobutylene, butadiene, 1-pentene, cyclopentene, 1-hexene, cyclohexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators of the present invention.

In most polymerization reactions the molar ratio of catalyst:polymerizable compounds employed is from $10^{-12}:1$ to $10^{-1}:1$, more preferably from $10^{-12}:1$ to $10^{-5}:1$.

The catalyst composition of the invention may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770. A more specific process is disclosed in copending application U.S. Ser. No. 08/10958, filed Jan. 29, 1993. The teachings of the foregoing publications and pending applications are hereby incorporated by reference.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution α-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins, preferably by supporting the catalyst composition by any suitable technique. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid or can be condensed to provide such a liquid, this can be suitably be fed to the bed to provide an evaporative cooling effect. Examples of olefin monomers which can be employed in this manner are olefins containing from about 3 to about eight, preferably from 3 to six carbon atoms. The volatile liquid evaporates in the hot fluidized bed to form gas which mixes with the fluidizing gas. If the volatile liquid is a monomer or comonomer, it may undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032, the teachings of which are also hereby incorporated by reference.

The polymerization reaction occurring in the gas fluidized bed is catalyzed by the continuous or semi-continuous addition of catalyst. Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with a dry inert gas such as nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. Where stated the term "room temperature" refers to a temperature from 20 to 25 C and the term "overnight" refers to a time from 12 to 18 hours.

EXAMPLES

Tris-(perfluorophenyl)borane (FAB) was obtained as a solid from Boulder Scientific Inc. and used without further purification. Modified methylaluminoxane (MMAO-3A) in heptane was purchased from Akzo-Nobel and methylaluminoxane (MAO) in toluene was purchased from Aldrich Chemical Co. Tris-(perfluorophenyl)aluminum (FAAL, as a toluene adduct) was prepared by exchange reaction between tris-(perfluorophenyl)borane and trimethylaluminum, reported by Biagini et.al., U.S. Pat. No. 5,602,269. All solvents were purified using the technique disclosed by Pangbom et al, *Organometallics*, 1996, 15, 1518–1520. All compounds and solutions were handled under an inert atmosphere (dry box). All chemical shift for $^{19}F$ NMR spectra were relative to a fixed external standard ($CFCl_3$) in benzene $d_6$ or toluene $d_8$, either of which were dried over N/K alloy and filtered prior to use. $^{1}H$ and $^{13}C$ NMR shifts were referenced to internal solvent resonances and are reported relative to TMS. In the formulas provided in the following examples, z' is intended to represent oligomer distribution and not stoichiometry. That is, mass balances are determined solely be reference to z and not z'.

Example 1

In a glove box, FAB (0.250 g, 0.488 mmol) was dissolved in 30 mL of dry toluene in a flask and MMAO-3A (5.59 mL, 0.56 M in heptane, 3.13 mmol, FAB/MMAO=1/6.4) was added dropwise. The reaction mixture was stirred for 2 h at room temperature giving a product mixture of the formula: $Ar_3Al)(AlQ^1_3)_{1.5}[(-AlQ^2-O-)_{2-30}]_{3.8}$(Ar=perfluorophenyl, $Q^1$ and $Q^2$=methyl and isobutyl). The solvent was removed under reduced pressure and the residue was dried in vacuo for a few hours to afford the product as a viscous oil (~0.42 g).

$^{1}H$ NMR ($C_7D_8$, 23° C.): δ−0.15 (br, —$AlQ^2$—O— backbone), −0.04 (s, br), 0.31 (d, br), 0.91 (d), and 1.83 (septet) for $Ar_3Al)(AlQ^1_3)_y$(Ar=perfluorophenyl, $Q^1$ and $Q^2$=methyl and isobutyl). $^{19}F$ NMR ($C_7D_8$, 23° C.) shows only broad peaks for one type of $AlC_6F_5$ resonance at δ−121.85 (s, br, 2 F, o-F), −151.78 (s, br, 1 F, p-F), −161.11 (s, br, 2 F, m-F).

Example 2

In a glove box, FAB (0.077 g, 0.15 mmol) was dissolved in 28 mL of dry toluene in a flask and MMAO-3A (1.43 mL, 0.56 M in heptane, 0.80 mmol, FAB/MMAO=1/5.3) was added dropwise. The reaction mixture was stirred for 2 h at room temperature giving a product mixture of the formula: $(Ar_3Al)(AlQ^1_3)_{1.1}[(-AlQ^2-O-)_{2-30}]_{3.2}$ (Ar=perfluorophenyl, $Q^1$ and $Q^2$=methyl and isobutyl). A $^{19}F$ NMR spectrum of an aliquot taken from the mixture indicated a formation of a single fluoroaryl aluminum species. The solvent was then removed under reduced pressure and the residue was dried under reduced pressure for a few hours to afford the product as a viscous oil (~0.071 g).

After isolation, $^{1}H$ NMR ($C_6D_6$, 23° C.): δ−0.14 (br, —$AlQ^2$—O— backbone), 0.15 (s, br), 0.30 (d, br), 0.94 (d), and 1.81 (septet) for $(Ar_3Al)(AlQ^1_3)_y$(Ar=perfluorophenyl, $Q^1$ and $Q^2$=methyl and isobutyl). $^{19}F$ NMR ($C_6D_6$, 23° C.) shows only broad peaks for one type of $AlC_6F_5$ resonance at δ−122.19 (d, br, 2 F, o-F), −150.92 (s, br, 1 F, p-F), −160.64 (s, br, 2 F, m-F).

Example 3

In a glove box, FAB (0.077 g, 0.15 mmol) was dissolved in 15 mL of dry hexane in a flask and MMAO-3A (1.145 mL, 0.56 M in heptane, 0.64 mmol, FAB/MMAO=1/4.2) was added dropwise. The reaction mixture was stirred for 2 h at room temperature giving a product mixture of the formula: $(Ar_3Al)(AlQ^1_3)_{0.7}[(AlQ^2-O-)_{2-30}]_{0.25}$ (Ar=perfluorophenyl, $Q^1$ and $Q^2$=methyl and isobutyl). The solvent was removed under reduced pressure and the residue was dried under reduced pressure for a few hours to afford the product as a viscous oil (~0.07 g).

$^{1}H$ NMR ($C_6D_6$, 23° C.): δ−0.13 (br, —$AlQ^2$—O— backbone), 0.06 (s, br), 0.36 (d, br), 0.95 (d), and 1.82 (septet) for $(Ar_3Al)(AlQ^1_3)_y$(Ar=perfluorophenyl, $Q^1$ and $Q^2$=methyl and isobutyl). $^{19}F$ NMR ($C_6D_6$, 23° C.) shows only broad peaks for one type of $AlC_6F_5$ resonance at δ−122.06 (s, br, 2 F, o-F), −150.84 (s, br, 1 F, p-F), −160.60 (s, br, 2 F, m-F).

Example 4

In a glove box, FAB (0.10 g, 0.195 mmol) was dissolved in 15 mL of dry toluene in a flask and MAO (1.29 mL, 10 percent by weight in toluene, d=0.875, 1.51 M, 1.95 mmol, FAB/MAO=1/10) was added dropwise. The reaction mixture was stirred for 4 h at room temperature giving a product mixture of the formula: $(Ar_3Al)(-AlQ^1_3)_{2.0}[(AlQ^2-O-)_{2-30}]_{7.0}$ (Ar=perfluorophenyl, $Q^1$ and $Q^2$=methyl and isobutyl). The solvent was removed under reduced pressure and the residue was dried under reduced pressure for a few hours to afford the product as a glassy solid.

$^{1}H$ NMR ($C_7D_8$, 23° C.): δ−0.13 (s, br). $^{19}F$ NMR ($C_7D_8$, 23° C.) shows only one type of $AlC_6F_5$ resonance at δ−122.12 (dd, 2 F, o-F), −151.83 (s, br, 1 F, p-F), −160.99 (t, 2 F, m-F).

Example 5

In a glove box, FAAL (10 mg, 0.016 mmol, toluene adduct) was dissolved in 0.7 mL of toluene-$d_8$ in a J-Young NMR tube and MAO (0.032 mL, 10 percent by weight in toluene, d=0.875, 1.51 M, 0.048 mmol, FAAL/MAO=1/3) was added. NMR spectra were recorded after mixing these reagents in the NMR tube for 1 h. $^{1}H$ NMR ($C_7D_8$, 23° C.): −0.07 ppm. $^{19}F$ NMR ($C_7D_8$, 23° C.): δ−122.15 (dd, 2 F, o-F), −151.57 (s, br, 1 F, p-F), −160.96 (t, 2 F, m-F). The data is consistent with the dynamic features of a mixture of the formula: $Ar_3Al)(AlMe_3)_{0.9}[(-AlMe-O-)_{2-30}]_{2.1}$. (Ar=perfluorophenyl).

Example 6

In a glove box, FAB (0.125 g, 0.24 mmol) was dissolved in 20 mL of dry hexane in a flask and MMAO-3A (2.79 mL, 0.56 M in heptane, 1.56 mmol, FAB/MMAO=1/6.5) was added dropwise. The reaction mixture was stirred for 2 h at room temperature giving a product mixture of the formula: $(Ar_3Al)(AlQ^1_3)_{1.6}[(-AlQ^2-O-)_{2-30}]_{3.9}$ (Ar= perfluorophenyl, $Q^1$ and $Q^2$=methyl and isobutyl). The solvent was removed under reduced pressure and the residue was dried under reduced pressure for a few hours to afford the product as a viscous oil (~0.13 g).

$^1$H NMR ($C_7D_8$, 23° C.): δ−0.18 (br, —AlQ$^2$—O— backbone), 0.02 (s, br), 0.24 (d, br), 0.95 (d), and 1.82 (septet) for (Ar$_3$Al) (AlQ$^1_3$)$_y$.(Ar=perfluorophenyl, Q$^1$and Q$^2$=methyl and isobutyl). $^{19}$F NMR ($C_7D_8$, 23° C.) shows only broad peaks for one type of AlC$_6$F$_5$ resonance at δ−121.89 (s, br, 2 F, o-F), −151.71(s, br, 1F, p-F), −160.99 (s, br, 2 F, m-F).

Example 7

In a glove box, FAB (0.50 g, 0.98 mmol) was dissolved in 40 mL of dry toluene in a flask and MMAO-3A (8.72 mL, 0.56 M in heptane, 4.88 mmol, FAB/MMAO=1/5) was added dropwise. The reaction mixture was stirred for 2 h at room temperature giving a product mixture of the formula: (Ar$_3$Al) (AlQ$^1_3$)$_1$. [(—AlQ$^2$—O—)$_{2-30}$]$_{3.0}$ (Ar=perfluorophenyl, Q$^1$ and Q$^2$=methyl and isobutyl). The solvent was removed under reduced pressure and the residue was dried under reduced pressure for a few hours to afford the product as a viscous oil (~0.84 g).

$^1$H NMR ($C_6D_6$, 23° C.): δ−0.05 (s, br), 0.28 (d, br), 0.95 (d), and 1.81 (septet) for (Ar$_3$Al) (AlQ$^1_3$)$_y$.(Ar=perfluorophenyl, Q$^1$ and Q$^2$=methyl and isobutyl). $^{19}$F NMR ($C_6D_6$, 23° C.) shows only broad peaks for one type of AlC$_6$F$_5$ resonance at δ−121.86 (s, br, 2 F, o-F), −151.40 (s, br, 1 F, p-F), −160.90 (s, br, 2 F, m-F).

Example 8

In a glove box, FAB (0.077 g, 0.15 mmol) was dissolved in 28.7 mL of dry isopar-E in a flask and MMAO-3A (1.34 mL, 0.56 M in heptane, 0.75 mmol, FAB/MMAO=1/5) was added dropwise. The reaction mixture was stirred for 2 h at room temperature and $^{19}$F NMR (in isopar E®) spectrum of an aliquot taken from the mixture indicated a formation of a single fluoroaryl aluminum species with very broad peaks for one type of AlC$_6$F$_5$ resonance at δ−122.20 (s, br, 2 F, o-F), −150.54 (s, br, W$_{1/2}$>167 Hz, 1 F, p-F), −159.95 (s, br, 2 F, m-F). All data are consistent with the dynamic features of this complex with a mixture of the formula: (Ar$_3$Al) (AlQ$^1_3$)$_{1.0}$[(—AlQ$^2$—O—)$_{2-30}$]$_{3.0}$. This solution was used for polymerization screening. For further characterization purpose, the solvent of the aliquot was removed under reduced pressure and the residue was dried under reduced pressure for a few hours to afford the product as a viscous oil. $^1$H NMR ($C_6D_6$, 23° C.): δ−0.02 (s, br), 0.37 (s, br), 0.95 (d), and 1.81 (septet) for for (Ar$_3$Al) (AlQ$^1_3$)$_y$.(Ar= perfluorophenyl, Q$^1$ and Q$^2$=methyl and isobutyl). $^{19}$F NMR ($C_6D_6$, 23° C.) shows only broad peaks for one type of AlC$_6$F$_5$ resonance at δ−122.08 (s, br, 2 F, o-F), −151.10 (s, br, 1 F, p-F), −160.81 (s, br, 2 F, m-F).

Example 9

In a glove box, FAB (0.077 g, 0.15 mmol) was dissolved in 27.4 mL of dry toluene in a flask and MMAO-3A (2.686 mL, 0.56 M in heptane, 1.50 mmol, FAB/MMAO=1/10) was added dropwise. The reaction mixture was stirred for 2 h at room temperature and $^{19}$F NMR (in toluene) spectrum of an aliquot taken from the mixture indicated a formation of a single fluoroaryl aluminum species with broad peaks for one type of AlC$_6$F$_5$ resonance at δ−121.66 (s, br, 2 F, o-F), −152.24 (s, br, 1 F, p-F), −161.24 (s, br, 2 F, m-F). All data are consistent with the dynamic features of this complex with a mixture of the formula: (Ar$_3$Al) (AlQ$^1_3$)$_{3.0}$ [(—AlQ$^2$—O—)$_{2-30}$]$_{6.0}$.(Ar=perfluorophenyl, Q$^1$ and Q$^2$=methyl and isobutyl).

Example 10

In a glove box, FAAL (0.020 g, 0.032 mmol, toluene adduct) was dissolved in 0.7 mL of toluene-d$_8$ in a J-Young NMR tube and MMAO-3A (0.0143 mL, 0.56M in heptane, 0.008 mmol, FAAL/MMAO=4/1) was added. NMR spectra were recorded after mixing these reagents in the NMR tube for 20 min. $^{19}$F NMR shows a mixture of two species. FAAL ($C_7D_8$, 23° C.): δ−122.91 (d, 2 F, o-F), −151.10 (t, 1 F, p-F), −160.83 (t, 2 F, m-F). (Ar$_3$Al) (AlQ$^1_3$)$_y$ (Ar= perfluorophenyl, Q$^1$ and Q$^2$=methyl and isobutyl). ($C_7D_8$, 23° C.): δ−121.68−122.16 (br, 2 F, o-F), −152.07 (br, 1 F, p-F), −161.42 (br, 2 F, m-F). NMR spectroscopic features of the product are consistent with a mixture of the formula: (Ar$_3$Al) (AlQ$^1_3$)$_{0.1}$[(—AlQ$^2$—O—)$_{2-30}$]$_{0.15}$.

Example 11

In a glove box, FAAL (0.005 g, 0.008 mmol, toluene adduct) was dissolved in 0.5 mL of toluene-d$_8$ in a J-Young NMR tube and MMAO-3A (0.0143 mL, 0.56 M, 0.008 mmol, FAAL/MMAO=1/1) was added. NMR spectra were recorded after mixing these reagents in the NMR tube for 20 min. NMR spectroscopic features of the product are consistent with a mixture of the formula: (Ar$_3$Al) (AlQ$^1_3$)$_{0.4}$ [(—AlQ$^2$—O—)$_{2-30}$]$_{0.6}$. (Ar=perfluorophenyl, Q$^1$ and Q$^2$=methyl and isobutyl).

Example 12

In a glove box, FAAL (0.040 g, 0.064 mmol, toluene adduct) was dissolved in 0.5 mL of toluene-d$_8$ in a J-Young NMR tube and MMAO-3A (0.0143 mL, 0.56 M, 0.008 mmol, FAAL/MMAO=8/1) was added. NMR spectra were recorded after mixing these reagents in the NMR tube for 20 min. NMR spectroscopic features of the product are consistent with a mixture of the formula: (Ar$_3$Al) (AlQ$^1_3$)$_{0.05}$ [(—AlQ$^2$—O—)$_{2-30}$]$_{0.08}$. (Ar=perfluorophenyl, Q$^1$and Q$^2$=methyl and isobutyl).

Polymerizations

A 2-liter Parr reactor was used in the polymerizations. All feeds were passed through columns of alumina and a decontaminant (Q-5® catalyst available from Englehardt Chemicals Inc.) prior to introduction into the reactor. Catalyst and cocatalysts are handled in a glovebox containing an atmosphere of argon or nitrogen.

A stirred 2.0 liter reactor is charged with about 740 g of Isopar-E™ mixed alkanes solvent (available from Exxon Chemicals Inc.) and 118 g of 1-octene comonomer. Hydrogen is added as a molecular weight control agent by differential pressure expansion from a 75 ml addition tank at 25 psi (2070 kPa). The reactor is heated to the polymerization temperature of 130° C. and saturated with ethylene at 500 psig (3.4 MPa). Catalyst ((t-butylamido) (tetramethylcyclopentadienyl)-dimethylsilanetitanium 1,3-pentadiene) (Boulder Scientific Inc.) and cocatalyst, as dilute solutions in toluene or in Isopar-E™, are mixed and transferred to a catalyst addition tank and injected into the reactor. The polymerization conditions are maintained for 15 minutes with ethylene added on demand. The resulting solution is removed from the reactor, quenched with isopropyl alcohol, and stabilized by addition of 10 ml of a toluene solution containing approximately 67 mg of a hindered phenol antioxidant (Irganox™ 1010 from Ciba Geigy Corporation) and 133 mg of a phosphorus stabilizer (Irgafos 168 from Ciba Geigy Corporation).

Between polymerization runs a wash cycle in which 850 g of mixed alkanes is added to the reactor and the reactor heated to 150° C. The reactor is emptied of the heated solvent immediately before beginning a new polymerization run.

Polymers are recovered by drying in a vacuum oven set at 140° C. for about 20 hours. Density values are derived by determining the polymer's mass when in air and when immersed in methylethyl ketone. Micro melt index values (MMI) are obtained using a "Custom Scientific Instrument Inc. Model CS-127MF-015" apparatus at 190° C. MMI (micro-melt index) are unit-less values calculated as follows: MMI=1/(0.00343 t−0.00251), where t=time in seconds. Results are contained in Table 1.

to a catalyst addition tank and injected into the reactor. The amount of catalyst used was 1.25 $\mu$M. The amount of cocatalyst used was 3.75 $\mu$M (based on FAB).

The polymerization conditions were maintained for the indicated times. The resulting solution is removed from the reactor, quenched with isopropyl alcohol, and stabilized by addition of 10 ml of a toluene solution containing approximately 67 mg of a hindered phenol antioxidant (Irganox™ 1010 from Ciba Geigy Corporation) and 133 mg of a phosphorus stabilizer (Irgafos 168 from Ciba Geigy Corporation). The polymers were recovered by devolatilization at 120° C. for approximately 20 hours. Results are contained in Table 2.

TABLE 1

| Run | Activator | catalyst/activator* | $\Delta$T (° C.) | Yield (g) | Efficiency (g polymer/$\mu$g Ti) | Density (g/ml) | MMI |
|---|---|---|---|---|---|---|---|
| A** | B—(C$_6$F$_5$)$_3$ | 1.5/1.5 | 6.0 | 85.5 | 1.19 | 0.898 | 4.2 |
| B** | B—(C$_6$F$_5$)$_3$ | 1.5/1.5 | 4.9 | 82.8 | 1.15 | 0.899 | 3.5 |
| 1 | Example 11 | 1/4 | 1.7 | 43.7 | 0.91 | 0.902 | 0.9 |
| 2 | Example 10 | 1/4 | 17.9 | 63.0 | 1.32 | 0.897 | 1.9 |
| 3 | Example 10 | 1/4 | 13.9 | 71.0 | 1.48 | 0.903 | 1.9 |
| 4 | Example 12 | 1/4 | 34.3 | 70.6 | 1.47 | 0.903 | 4.6 |
| 5 | Example 12 | 0.5/2 | 16.5 | 69.6 | 2.91 | 0.902 | 2.6 |
| 6 | Example 12 | 0.25/1 | 4.9 | 50.5 | 4.22 | 0.900 | 1.8 |
| 7 | Example 1 | 1/3 | 3.9 | 115.9 | 2.42 | 0.895 | 0.4 |
| 8 | Example 1 | 1/3 | 3.1 | 126.4 | 2.64 | 0.895 | 0.4 |
| 9 | Example 2 | 1/3 | 27.9 | 163.8 | 3.42 | 0.874 | 2.2 |
| 10 | Example 2 | 0.5/1.5 | 15.1 | 159.1 | 6.65 | 0.878 | 2.2 |
| 11 | Example 2 | 0.25/0.75 | 1.3 | 99.1 | 8.28 | 0.898 | 0.7 |
| 12 | Example 8 | 0.5/1.5 | 1.8 | 142.8 | 5.96 | 0.891 | 0.9 |
| 13 | Example 8 | 0.5/1.5 | 1.9 | 147.2 | 6.15 | 0.891 | 1.0 |
| 14 | Example 9 | 0.5/1.5 | 1.6 | 45.8 | 1.91 | 0.895 | 0.3 |
| C** | FAAL | 0.5/0.5 | 0.0 | 0.9 | 0.04 | — | — |
| D** | FAAL | 0.25/1 | 1.3 | 0.1 | — | — | — |

*$\mu$mole catalyst/$\mu$mole activator based on B(C$_6$F$_5$)$_3$ or Al(C$_6$F$_5$)$_3$
**comparative, not an example of the invention

TABLE 2

| Run | T (° C.) | H$_2$ (kPa) | Time (min.) | Efficiency (g poly./mg Zr) | Mn | Mw | Tm (° C.) |
|---|---|---|---|---|---|---|---|
| 15 | 100 | 0 | 20 | 470 | 83500 | 167000 | 152.6 |
| 16 | 100 | 70 | 10 | 606 | 54200 | 99200 | 151.9 |
| 17 | 90 | 0 | 16 | 192 | 111000 | 232000 | 152.5 |
| 18 | 90 | 70 | 13 | 349 | 87500 | 163000 | 153.8 |

Propylene Homopolymerization

The previous polymerization conditions were substantially repeated using the same 2-liter Parr reactor charged with about 625 g of Isopar-E™ mixed alkanes solvent and 150 g of propylene. Hydrogen, where used, was added as a molecular weight control agent by differential pressure expansion from a 75 ml addition tank at 10 psi (70 kPa). The reactor was heated to the indicated polymerization temperature (90 or 100° C.) and catalyst (rac-dimethylsilane bis(2-methyl-4-phenylindenyl)zirconium 1,4-diphenylbutadiene, prepared according to U.S. Pat. No. 5,616,664, ) and cocatalyst (a mixture of trispentafluorophenylborane (FAB) and MMAO-3A premixed for 15 minutes in a molar ratio of 1:3), as dilute solutions in Isopar-E™, are mixed and transferred Example 13

In a glove box, FAAL (0.032 $\mu$mol, toluene adduct) was dissolved in 0.7 mL of benzene-d$_6$ in a J-Young NMR tube and MMAO-3A (4 $\mu$mol, FAAL/MMAO=8/1) was added. The NMR spectroscopic features of the product were consistent with a mixture of the formula: (Ar$_3$Al) (AlQ$^1_3$)$_{0.05}$ (—AlQ$^2$—O—)$_{0.08}$, where Ar is pentafluorophenyl and Q$^1$ and Q$^2$ are methyl or isopropyl. The metal complex (t-butylamido) (tetramethylcyclopentadienyl) dimethylsilanetitanium dimethyl, (8 $\mu$mol) was added to the above solution and the resulting mixture immediately turned to orange color. NMR spectroscopic features of the major product are consistent with a $\mu$-bridged bisadduct of the formula: Me$_2$Si($\eta^5$-Me$_4$C$_5$)(t-BuN)Ti[($\mu$-Me)Al(C$_6$F$_5$)$_3$]$_2$.

Example 14

The reaction conditions of Example 13 were substantially repeated excepting that the metal complex, rac-dimethylsilyl-bis(1-indenyl)zirconium dimethyl, (8 μmol) was added to activator mixture. The resulting mixture immediately turned to a deep red color. NMR spectroscopic features of the major product were consistent with a μ-bridged bisadduct of the formula, rac-Me$_2$Si($\eta^5$-Ind)$_2$Zr[(μ-Me)Al(C$_6$F$_5$)$_3$]$_2$.

What is claimed is:

1. A composition comprising a mixture of aluminum containing Lewis acids said mixture corresponding to the formula:

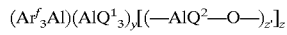

where;

Ar$^f$ is a fluorinated aromatic hydrocarbyl moiety of from 6 to 30 carbon atoms;

Q$^1$ is C$_{1-20}$ alkyl;

Q$^2$ is C$_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more Q$^2$ groups may be covalently linked with each other to form one or more fused rings or ring systems;

y is a number from 0 to 3.0; and z is a number from 0.01 to 10; and the moiety (—AlQ$^2$—O—)$_{z'}$ is a cyclic or linear oligomer with a repeat unit, z', of 2–30.

2. A composition comprising a mixture of aluminum containing Lewis acids said mixture corresponding to the formula:

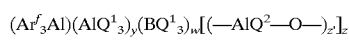

where;

Ar$^f$ is a fluorinated aromatic hydrocarbyl moiety of from 6 to 30 carbon atoms;

Q$^1$ is C$_{1-20}$ alkyl;

Q$^2$ is C$_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more Q$^2$ groups may be covalently linked with each other to form one or more fused rings or ring systems;

w is a number greater than or equal to 0 and less than or equal to y;

y is a number from 0 to 3.0; and z is a number from 0.05 to 10; and the moiety (—AlQ$^2$—O—) is a cyclic or linear oligomer with a repeat unit, z', of 2–30.

3. A composition comprising a mixture of aluminum containing Lewis acids said mixture corresponding to the formula:

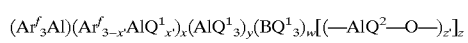

where;

Ar$^f$ is a fluorinated aromatic hydrocarbyl moiety of from 6 to 30 carbon atoms;

Q$^1$ is C$_{1-20}$ alkyl;

Q$^2$ is C$_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more Q$^2$ groups may be covalently linked with each other to form one or more fused rings or ring systems;

w is a number greater than or equal to 0 and less than or equal to y;

x' is 1 or 2, x is a number from 0 to 0.1;

y is a number from 0 to 3.0;

z is a number from 0.05 to 10; and the moiety (—AlQ$^2$—O—) is a cyclic or linear oligomer with a repeat unit, z', of 2–30.

4. A compound corresponding to the formula [Ar$^f_y$Al$_2$Q$^1_{(6-y)}$][(—AlQ$^2$—O—)$_{z'}$]$_z$, wherein Ar$^f$, Q$^1$ Q$^2$, y, z' and z are as defined in claim 1.

5. A composition or compound according to any one of claims 1–4, wherein Ar$^f$ is pentafluorophenyl, and Q$^1$ and Q$^2$ are C$_{1-4}$ alkyl.

6. A composition or compound according to any one of claims 1–4 wherein Ar$^f$ is pentafluorophenyl, and Q$^1$ and Q$^2$ are methyl and isobutyl.

7. A catalyst composition that is activated for polymerization of olefins comprising a metal complex and an activator which is the composition or compound according to claim 1, the molar ratio of metal complex to activator composition being from 0.1:1 to 3:1.

8. The catalyst composition of claim 7 wherein the metal complex is a Group 4 metal complex.

9. The catalyst composition of claim 7 wherein the molar ratio of metal complex to activator composition is from 0.2:1 to 2:1.

10. The catalyst composition of claim 7 additionally comprising a solid, particulated support.

11. The catalyst composition of claim 7 wherein the metal complex is:

(tert-butylamido)(tetramethylcyclopentadienyl) dimethylsilanetitanium dimethyl, (tert-butylamido)(tetramethylcyclopentadienyl) dimethylsilanetitanium 1,3-pentadiene, (tert-butylamido)(2-methyl-s-indacen-1-yl) dimethylsilanetitanium 1,3-pentadiene, (tert-butylamido)(3-(N-pyrrolidinyl)inden-1-yl) dimethylsilanetitanium 1,3-pentadiene, (tert-butylamido)(3,4-cyclopenta(/)phenanthren-2-yl) dimethylsilanetitanium 1,4-diphenyl-1,3-butadiene, (dimethylsilyl-bis-2-methyl-4-phenylindenyl)zirconium dimethyl, (dimethylsilyl-bis-2-methyl-4-phenylindenyl)zirconium 1,4-diphenyl-1,3-butadiene,
(dimethylsilyl)bis(inden-1-yl)zirconium dimethyl,
(1,2-ethanediyl)bis(inden-1-yl)zirconium dimethyl, or
(1,2-ethanediyl)bis(inden-1-yl)zirconium 1,4-diphenyl-1,3-butadiene.

12. A process for polymerization of one or more addition polymerzable monomers comprising contacting the same, optionally in the presence of an inert aliphatic, alicyclic or aromatic hydrocarbon, with the catalyst composition according to any one of claims 7–11.

13. The process of claim 12 wherein one or more α-olefins having from 2 to 20,000 carbon atoms are polymerized.

14. The process according to claim 12 which is a gas phase polymerization of one or more $C_{2-6}$ olefins.

15. The process according to claim 12 which is a slurry polymerization of a $C_{2-20}$ olefin, diolefin, cycloolefin or mixture thereof.

* * * * *